United States Patent
Tseng et al.

(10) Patent No.: US 8,121,303 B2
(45) Date of Patent: Feb. 21, 2012

(54) STETHOSCOPE CAPABLE OF ELIMINATING UNWANTED SOUNDS AND METHOD THEREOF

(75) Inventors: Kuo-Hua Tseng, Yilan County (TW); Yu-Kon Chou, Taipei County (TW); Pei-Ying Shieh, Hsinchu (TW); Wen-Yang Chou, Zhubei (TW); Mao-Shun Su, Yilan County (TW); Tsung-Ter Kuo, Taichung County (TW)

(73) Assignee: Industrial Technology Research Institute, Hsinchu (TW)

( * ) Notice: Subject to any disclaimer, the term of this patent is extended or adjusted under 35 U.S.C. 154(b) by 1349 days.

(21) Appl. No.: 11/448,720

(22) Filed: Jun. 8, 2006

(65) Prior Publication Data

US 2007/0154023 A1    Jul. 5, 2007

(30) Foreign Application Priority Data

Dec. 30, 2005 (TW) .............................. 94147671 A

(51) Int. Cl.
*A61B 7/04* (2006.01)
(52) U.S. Cl. ........................................ 381/67; 381/71.13
(58) Field of Classification Search .................. 381/67, 381/71.6, 71.7, 71.13, 72; 434/266, 262, 434/267, 270, 307, 318, 365, 396; 327/141, 327/297, 341, 20
See application file for complete search history.

(56) References Cited

U.S. PATENT DOCUMENTS

| | | | |
|---|---|---|---|
| 6,220,866 B1 * | 4/2001 | Amend et al. | 434/266 |
| 6,661,897 B2 * | 12/2003 | Smith | 381/67 |
| 2003/0002685 A1 * | 1/2003 | Werblud | 381/67 |
| 2003/0128847 A1 * | 7/2003 | Smith | 381/67 |
| 2004/0105556 A1 * | 6/2004 | Grove | 381/67 |
| 2005/0157888 A1 | 7/2005 | Yang | |

FOREIGN PATENT DOCUMENTS

CN    2168285 Y    6/1994

* cited by examiner

*Primary Examiner* — Xu Mei
*Assistant Examiner* — Leshui Zhang
(74) *Attorney, Agent, or Firm* — Birch, Stewart, Kolasch & Birch, LLP

(57) ABSTRACT

A stethoscope capable of eliminating unwanted sounds and method thereof, the stethoscope and method thereof mainly use a stethoscope head containing a sensor and a signal processing circuit. By way of detecting and judging whether the stethoscope head arrives on correct stethoscopic position by the sensor, unwanted sounds generating by frictions, translations, or collisions during the stethoscopic process can be effectively eliminated such that the stethoscopic quality can be improved. Thus, a doctor can use less time and spirit to make a correct diagnosis for a patient with least unwanted interference sounds.

20 Claims, 4 Drawing Sheets

STETHOSCOPE CAPABLE OF ELIMINATING UNWANTED SOUNDS AND METHOD THEREOF

FIELD OF THE INVENTION

The present invention relates to a stethoscope capable of eliminating unwanted sounds, and more particularly, to stethoscope capable of effectively eliminating unwanted sounds generating by frictions, translations, or collisions during an auscultatory process for improving auscultation quality by the use of a stethoscope head containing a sensor and a signal processing circuit.

BACKGROUND OF THE INVENTION

Analysis of heart, lung and vascular disorders by means of noninvasive auscultation has long been a very useful tool for medical diagnosis of ailments. By using a stethoscope, a physician would listen to the heart sounds, chest sounds or other body sounds to identify sounds associated with abnormalities. The stethoscope has proven to be a valuable instrument for the transmission of these sounds to the examining physician. However, identifying specific murmurs, like identifying heart sounds, is difficult. Developing the skill to make a proper analysis takes years of study and practice. In addition, it has been recognized that there is a need for amplifying certain frequency areas relative to those which are effectively reproduced by a stethoscope so as to provide physicians with improved sound quality for enhancing diagnosis of abnormalities.

Conventional stethoscope had been invented and used for over 190 years since Year 1816 while electronic stethoscopes was developed not until Year 1922. Modern electronic stethoscopes can improve sound quality and provide visual indication of heart sounds or chest sounds, such as cardiophonography. However, early electronic stethoscopes, which are composed of vacuum tubes or transistors, are typically expensive and bulkier than conventional stethoscopes. Accordingly, electronic stethoscopes can only begin to replace the dominant role of conventional stethoscopes after the rapid development of IC technology at the end of $20^{th}$ century. Nevertheless, most electronic stethoscopes currently available on the market are analog electronic stethoscopes that are still lacking of the convenient of a conventional stethoscope.

In a prior-art electronic stethoscope disclosed in U.S. Pub. No. 2005/0157888 A1, entitled "Electronic Stethoscope with Piezo-Electrical Film Contact Microphone", the auscultatory sounds are first being amplified and then the amplified sounds are sent to a filter for eliminating unwanted sounds. Although the aforesaid electronic stethoscope is able to eliminate unwanted sound in an auscultatory process, it is still imperfect that the elimination is realized by a very complex signal processing operation and apparatuses, and a physician using the referring stethoscope to perform an auscultatory process is still bothered by ambient noises, e.g. a bumping sound of a collision happening in the vicinity of the auscultatory being performed.

Therefore, it is in need of a stethoscope capable of effectively eliminating unwanted sounds generating by frictions, translations, or collisions during an auscultatory process for improving auscultation quality by the use of a stethoscope head containing a sensor and a signal processing circuit, such that a physicians can exercise a diagnosis of abnormalities with less effort and time and without being interfered by noises.

SUMMARY OF THE INVENTION

The primary object of the present invention is to provide a stethoscope capable of effectively eliminating unwanted sounds in an auscultatory process, which utilizes a sensor and signal processing circuit embedded in a stethoscope head of the stethoscope to determine whether the stethoscope head is located at a proper position for the auscultatory process while effectively eliminating unwanted sounds generating by frictions, translations, or collisions during the auscultatory process.

It is another object of the invention to provide a stethoscopic method with noise elimination ability, which is characterized in that: the tilting of a stethoscope head or the angular variation of the stethoscope head per time unit is detected and measured by a sensor embedded inside the stethoscope head; an evaluation is made using a polling means for determining whether the detected angular velocity or the inclination angle is larger than a threshold value; if so, a stethoscope is enabled to stop the gathering of auscultatory sounds or enter a power-saving mode as it is determined that the stethoscope head is not located at a proper position for an auscultatory process to be performed; otherwise, the stethoscope is enabled to start the gathering of auscultatory sounds for performing the auscultatory process while unwanted sounds generating by frictions, translations, or collisions are eliminated.

To achieve the above objects, the present invention provides a stethoscope apparatus and method, which are capable of effectively eliminating unwanted sounds generating by frictions, translations, or collisions during an auscultatory process for improving auscultation quality by the use of a stethoscope head containing a sensor and a signal processing circuit, such that a physicians can exercise a diagnosis of abnormalities with less effort and time and without being interfered by noises.

Other aspects and advantages of the present invention will become apparent from the following detailed description, taken in conjunction with the accompanying drawings, illustrating by way of example the principles of the present invention.

DESCRIPTION OF THE PREFERRED EMBODIMENT

For your esteemed members of reviewing committee to further understand and recognize the fulfilled functions and structural characteristics of the invention, several preferable embodiments cooperating with detailed description are presented as the follows.

Figure 1:
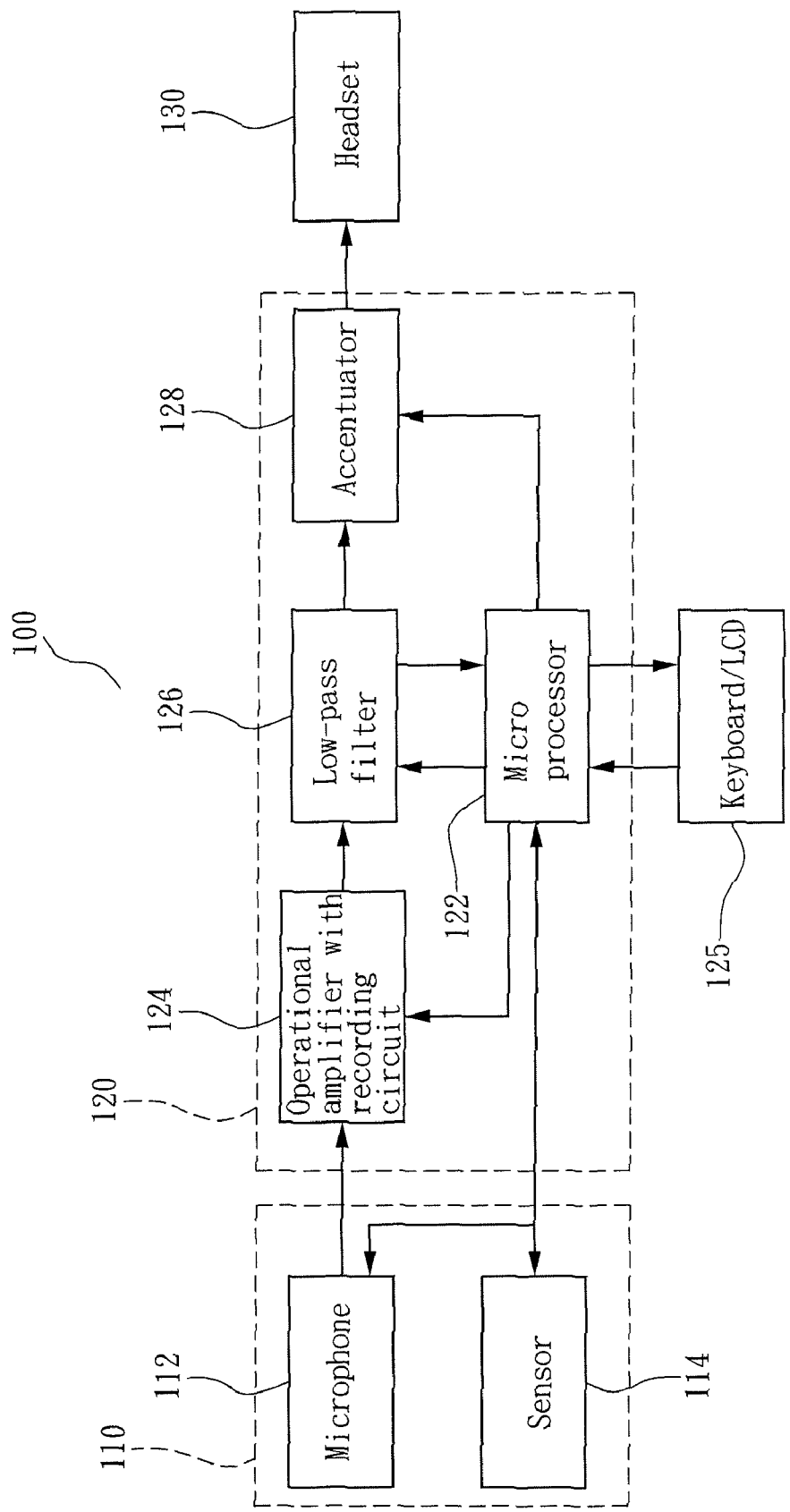
FIG. 1 shows a stethoscope capable of eliminating unwanted sounds according to the present invention.

Please refer to FIG. 1, which shows a stethoscope capable of eliminating unwanted sounds according to the present invention. The stethoscope 100 is comprised of: a stethoscope head 110, a signal processing circuit 120 and a headset 130.

Wherein. The stethoscope head 110 further comprises a microphone 112 and a sensor 114; the signal processing circuit 120 further comprises: a micro processor 122, an operational amplifier with recording circuit 124, a low-pass filter 126 and an accentuator 128. The micro processor 122 is capable of controlling the operations of the operational amplifier with recording circuit 124, the low-pass filter 126, the accentuator 128, the sensor 114, and the microphone 112 while connecting thereto, and simultaneously is polling the detection of the sensor 114 actively at any time for using the result of the detection to control the starting/stopping of the gathering of the auscultatory sound by the microphone 112. Moreover, the micro processor 122 can also be connected to a keyboard/LCD 125 for using the same as I/O device. If the detection of the sensor 114 satisfies a specific condition for enabling the gathering of the auscultatory sound, the stethoscope head 110 is assumed to be placed exactly at a specific position suitable for an auscultatory process to be performed. During the auscultatory process, the auscultatory sound, gathered by the microphone 112, amplified by the operational amplifier 124, filtered by the low-pass filter 126, and having one's characteristics frequency band being emphasized by the accentuator 128, is sent to the headset 130 to be used by a physician in an auscultatory process.

Figure 2:
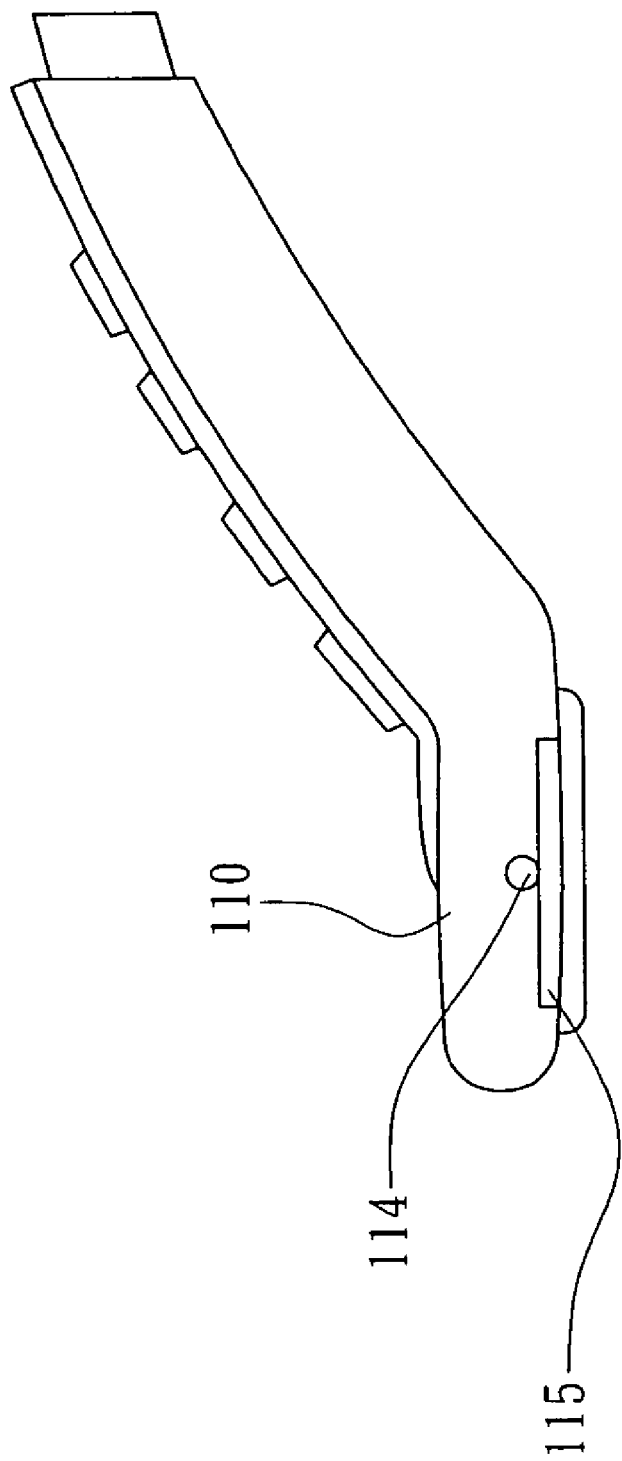
FIG. 2 is a schematic diagram showing a sensor of a stethoscope capable of eliminating unwanted sounds according to a first preferred embodiment of the present invention.

Please refer to FIG. 2, which is a schematic diagram showing a sensor of a stethoscope capable of eliminating unwanted sounds according to a first preferred embodiment of the present invention. In FIG. 2, the sensor 114 is an angular velocity sensor being positioned directly on a printed circuit board (PCB) 115, and is enabled to detect an angular variation measured between a specific position where the auscultatory process is performed and a planar surface where the sensor 114 is placed, while comparing the detected angular variation with a threshold value configured in the sensor 114 to determine whether the stethoscope head 114 is located at the specific position suitable for an auscultatory process to be performed. In a preferred aspect, if the detected angular variation is larger than the threshold value, the stethoscope head 110 is assumed to be still in the process of moving toward the specific position and not yet arrive, and thus the gathering of the auscultatory sound is stopped for eliminating unwanted sounds to be received thereby; if the detected angular variation is smaller than the threshold value, the stethoscope head 110 is assumed to be placed exactly at the specific position, and thus the gathering of the auscultatory sound is started.

Furthermore, the sensor 114 of FIG. 2 can be an angle sensor, which is capable of detecting an inclination angle measured between a planar surface where the sensor is placed and a reference position, while comparing the detected angle with a threshold value to determine whether the stethoscope head 114 is located at the specific position of the auscultatory process. In a preferred aspect, if the detected inclination angle is larger than the threshold value, the stethoscope head 110 is assumed to be placed on a table and not being used in an auscultatory process, and thus the gathering of the auscultatory sound is stopped for saving power; if the detected inclination angle is smaller than the threshold value, the stethoscope head 110 is assumed to be used in an auscultatory process, and thus the gathering of the auscultatory sound is started. In addition, the sensor 114 of FIG. 2 can be a pressure sensor, which is capable of detecting a pressure difference between the pressure measured at a specific position where the auscultatory process is performed and that at a planar surface where the sensor is placed, while comparing the pressure difference with a threshold value to determine whether the stethoscope head 114 is located at the specific position of the auscultatory process. In a preferred aspect, if the detected pressure difference is smaller than the threshold value, the stethoscope head 110 is assumed to be still in the process of moving toward the specific position and not yet arrive, and thus the gathering of the auscultatory sound is stopped for saving power; if the detected angular pressure variation is larger than the threshold value, the stethoscope head 110 is assumed to be placed exactly at the specific position, and thus the gathering of the auscultatory sound is started.

Figure 3:
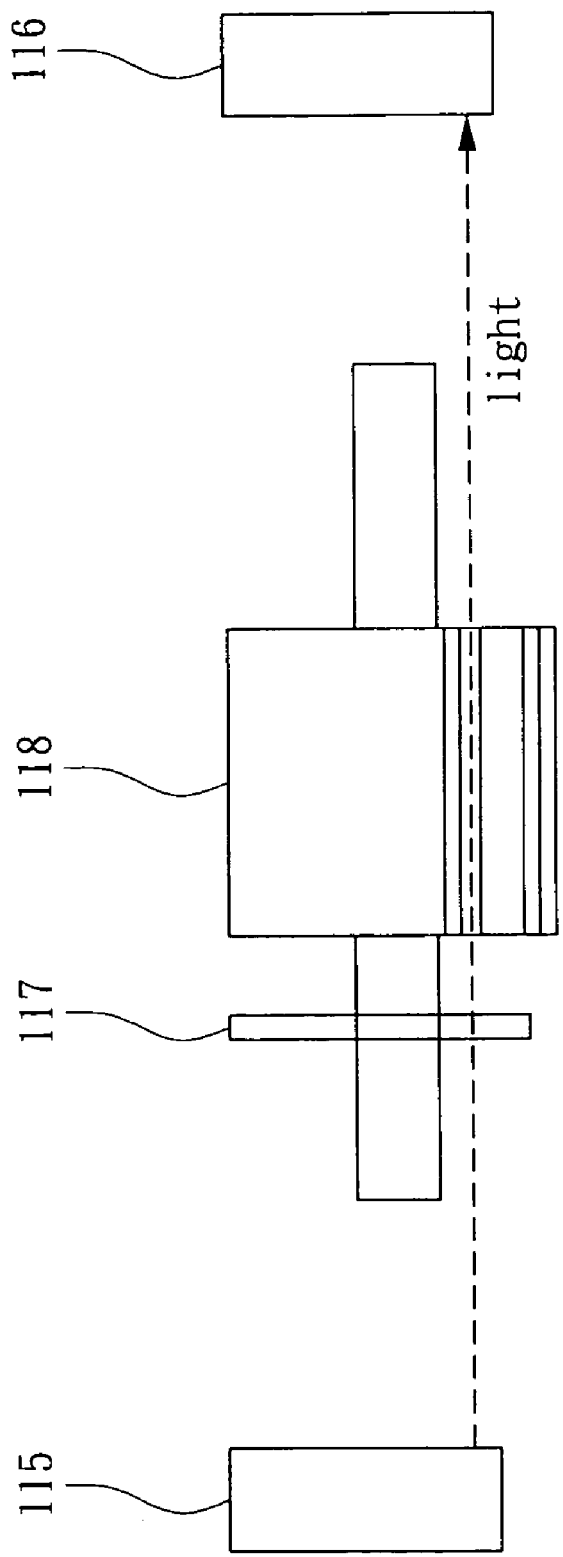
FIG. 3 is a schematic diagram showing a sensor of a stethoscope capable of eliminating unwanted sounds according to a second preferred embodiment of the present invention.

Please refer to FIG. 3, which is a schematic diagram showing a sensor of a stethoscope capable of eliminating unwanted sounds according to a second preferred embodiment of the present invention. In FIG. 3, the sensor 114 is an optical sensor, being comprised of a light emitter 115, a light receiver 116, a light grating 117 and a roller 118. Wherein, the light emitter 115 is used for discharging a light beam; the light receiver 116 is used for receiving the light beam and thus is positioned at a location corresponding to that of the light emitter 115; the light grating 117 is sandwiched between the light emitter 115 and the light receiver 116 to be used for controlling the propagation of the light beam; and the roller 118 is connected to the light grating while being sandwiched between the light emitter 115 and the light receiver 116. As the moving of the stethoscope head 110 is bringing along the roller 118 to enable the light grating 117 to rotate therewith, the optical sensor is enabled to measure a variation of continuity as it is detecting the propagating of the light beam passing through the rotating light grating 117 so as to use the measured variation of continuity for enabling the micro processor 122 to determine whether the stethoscope head 110 is located at the specific position suitable for an auscultatory process to be performed.

Figure 4:
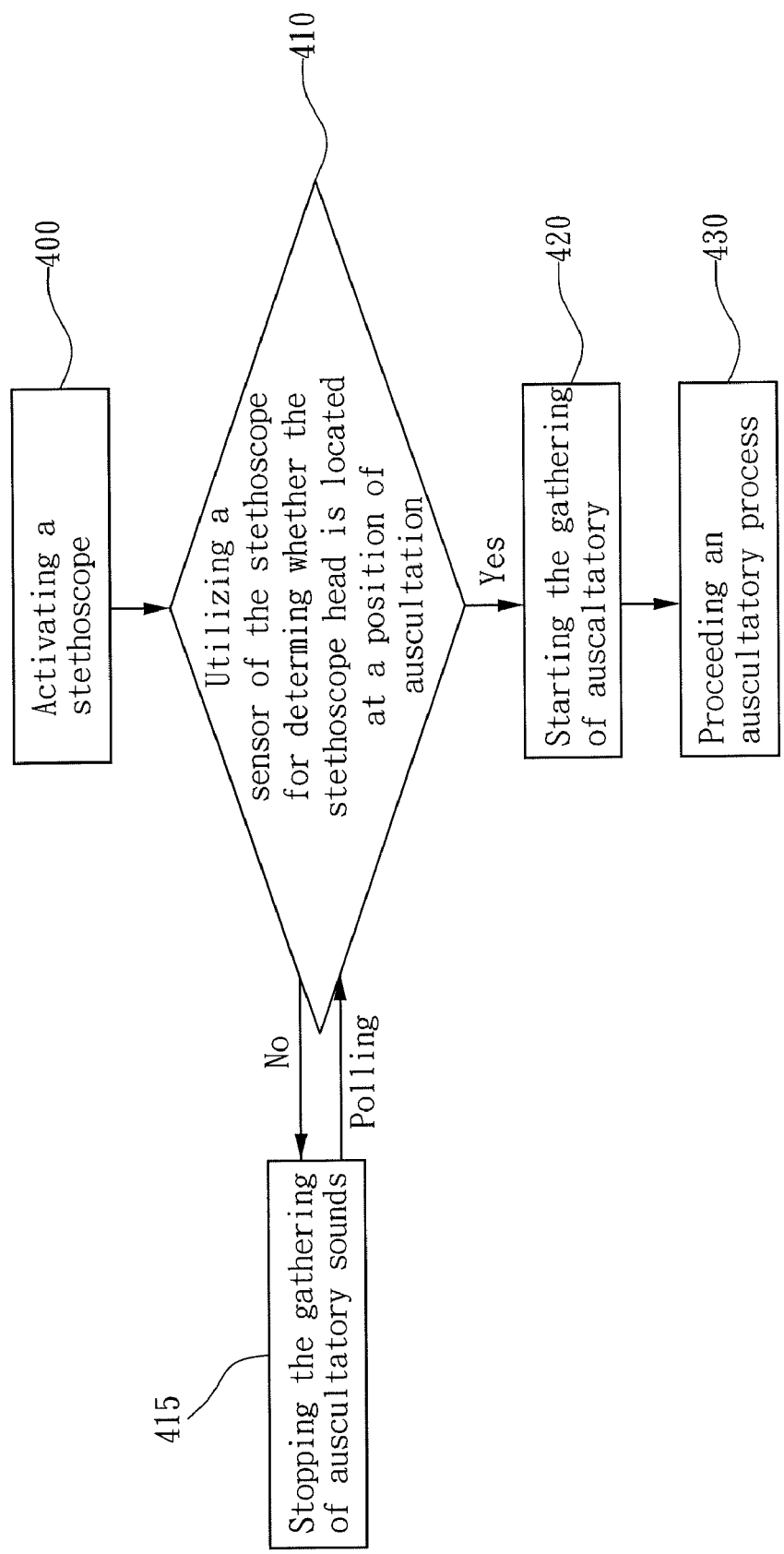
FIG. 4 is a flow chart illustrating the steps of a stethoscopic method of the present invention.

Please refer to FIG. 4, which is a flow chart illustrating the steps of a stethoscopic method of the present invention. The flow starts at step 400. At step 400, a stethoscope is activated, and then the flow proceeds to step 410. At step 410, a sensor of the stethoscope compares a value detected thereby with a designated threshold value to determine whether the stethoscope head is located at a specific position suitable for an auscultatory process to be performed; if so, the flow proceeds to step 420; otherwise, the flow proceeds to step 415. In step 415, the gathering of an auscultatory sound is stopped while a micro processor is enabled to keep on pulling the detection result of the sensor; if a latest pulling specified that the stethoscope head is located at a specific position suitable for an auscultatory process to be performed, the flow proceeds back to step 410. At step 420, the gathering of the auscultatory sound is started, and then the flow proceeds to step 430. At step 430, an auscultatory process can be performed.

To sum up, the present invention provides a stethoscope apparatus and method, which are capable of effectively eliminating unwanted sounds generating by frictions, translations, or collisions during an auscultatory process for improving auscultation quality by the use of a stethoscope head containing a sensor and a signal processing circuit, such that a physicians can exercise a diagnosis of abnormalities with less effort and time and without being interfered by noises.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A stethoscope capable of eliminating unwanted sounds, comprising:
   a stethoscope head, further comprising:
      a microphone, for gathering an auscultatory sound; and
      a sensor, for detecting and determining whether the stethoscope head is moving toward a specific position and whether the stethoscope head is located at a specific position for an auscultatory process to be performed, and for detecting and determining whether the stethoscope is moving toward a specific position;
   a signal processing circuit, connected to the stethoscope head for processing the auscultatory sound signal being gathered, further comprising:
      an operational amplifier with a recording circuit, for amplifying the auscultatory sound signal being gathered;
      a low-pass filter, for filtering out unwanted sound signals from the amplified auscultatory sound signal being gathered;
      an accentuator, for emphasizing characteristics of a frequency band of the low-pass filtered auscultatory sound signal being gathered; and
      a micro processor, for controlling the operations of the operational amplifier with the recording circuit, the low-pass filter, the accentuator, the sensor, and the microphone while connecting directly connected to the operational amplifier, the recording circuit, the low-pass filter, the accentuator, the sensor, and the microphone for controlling operation of the microphone; and
   a headset, connected to the signal processing circuit, for transmitting the auscultatory sound signal processed thereby to a user to be employed in the auscultatory process;
   wherein, the micro processor is polling a detection of the sensor actively at any time for using the result of the detection of the sensor to automatically control start or stop of the gathering of the auscultatory sound by the microphone based on the result of the detection of the sensor.

2. The stethoscope of claim 1, wherein the sensor is an angular velocity sensor capable of detecting an angular variation measured between a specific position where the auscultatory process is performed and a planar surface where the sensor is placed, while comparing the detected angular variation with a threshold value to determine whether the stethoscope head is located at the specific position of the auscultatory process.

3. The stethoscope of claim 1, wherein the sensor is an angle sensor capable of detecting an inclination angle measured between a planar surface where the sensor is placed and a reference position, while comparing the detected inclination angle with a threshold value to determine whether the stethoscope head is located at a specific position of the auscultatory profess.

4. The stethoscope of claim 1, wherein the sensor is a pressure sensor capable of detecting a pressure difference between the pressure measured at a specific position where the auscultatory process is performed and that at a planar surface where the sensor is placed, while comparing the pressure difference with a threshold value to determine whether the stethoscope head is located at a specific position of the auscultatory process.

5. The stethoscope of claim 1, wherein the sensor is an optical sensor further comprising:
   a light emitter, for discharging a light beam;
   a light receiver, for receiving the light beam while being positioned at a location corresponding to that of the light emitter;
   a light grating, sandwiched between the light emitter and the light receiver, for controlling propagation of the light beam; and
   a roller, connected to the light grating while being sandwiched between the light emitter and the light receiver,
   while, the optical sensor being enabled to measure a variation of continuity as it is detecting the propagating of the light beam passing through the light grating, for using the measured variation of continuity to determine whether the stethoscope head is located at a specific position of the auscultatory process.

6. The stethoscope of claim 1, wherein the auscultatory sound is generated by biological activity of an organ of a patient selected from the group consisting of the heart, the lung and the bowel.

7. The stethoscope of claim 2, wherein the auscultatory sound is generated by biological activity of an organ of a patient selected from the group consisting of the heart, the lung and the bowel.

8. The stethoscope of claim 3, wherein the auscultatory sound is generated by biological activity of an organ of a patient selected from the group consisting of the heart, the lung and the bowel.

9. The stethoscope of claim 4, wherein the auscultatory sound is generated by biological activity of an organ of a patient selected from the group consisting of the heart, the lung and the bowel.

10. The stethoscope of claim 5, wherein the auscultatory sound is generated by biological activity of an organ of a patient selected from the group consisting of the heart, the lung and the bowel.

11. A stethoscopic method capable of eliminating unwanted sounds, comprising steps of:
   activating a stethoscope;
   utilizing a sensor of the stethoscope to detect and determine whether a stethoscope head is located at a specific position for an auscultatory process to be performed, and to detect and determine whether the stethoscope is moving toward the specific position;
   automatically stopping the gathering of an auscultatory sound while enabling a micro processor to keep on pulling the detection result of the sensor as the stethoscope head is determined to be not located at the specific position of the auscultatory process;
   directly connecting the micro processor to a microphone for controlling operation of the microphone;
   automatically starting the gathering of the auscultatory sound from the microphone by using the micro processor as the stethoscope head is determined to be located at the specific position of the auscultatory process; and
   proceeding the auscultatory process and wherein the auscultatory process comprising
   gathering an auscultatory sound by the microphone;
   amplifying the auscultatory sound signal being gathered;
   low-pass filtering the amplified auscultatory sound signal being gathered;
   emphasizing characteristics of a frequency band of the low pass filtered auscultatory sound signal being gathered;

transmitting the emphasized auscultatory sound signal being gathered to a user by a headset.

12. The stethoscopic method of claim 11, wherein the sensor is an angular velocity sensor capable of detecting an angular variation measured between a planar surface where the sensor is placed and a planar surface where the sensor is placed, while comparing the detected angular variation with a threshold value to determine whether the stethoscope head is located at the specific position of the auscultatory process.

13. The stethoscopic method of claim 11, wherein the sensor is an angle sensor capable of detecting an inclination angle measured between a specific position where the auscultatory process is performed and a reference position, while comparing the detected angle with a threshold value to determine whether the stethoscope head is located at the specific position of the auscultatory process.

14. The stethoscopic method of claim 11, wherein the sensor is a pressure sensor capable of detecting a pressure differ nee between the pressure measured at a specific position where the auscultatory process is performed and that at a planar surface where the sensor is placed, while comparing the pressure difference with a threshold value to determine whether the stethoscope head is located at the specific position of the auscultatory process.

15. The stethoscopic method of claim 11, wherein the sensor is an optical sensor capable of measure a variation of continuity as it is detecting propagating of a light beam passing through a light grating, while using the measured variation of continuity to determine whether the stethoscope head is located at the specific position of the auscultatory process.

16. The stethoscopic method of claim 11, wherein the auscultatory sound is generated by biological activity of an organ of a patient selected from the group consisting of the heart, the lung and the bowel.

17. The stethoscopic method of claim 12, wherein the auscultatory sound is generated by biological activity of an organ of a patient selected from the group consisting of the heart, the lung and the bowel.

18. The stethoscopic method of claim 13, wherein the auscultatory sound is generated by biological activity of an organ of a patient selected from the group consisting of the heart, the lung and the bowel.

19. The stethoscopic method of claim 14, wherein the auscultatory sound is generated by biological activity of an organ of a patient selected from the group consisting of the heart, the lung and the bowel.

20. The stethoscopic method of claim 15, wherein the auscultatory sound is generated by biological activity of an organ of a patient selected from the group consisting of the heart, the lung and the bowel.

* * * * *